United States Patent [19]
Gerhardson et al.

[11] Patent Number: 5,900,236
[45] Date of Patent: May 4, 1999

[54] COMPOSITION AND METHOD FOR CONTROLLING PLANT DISEASES USING *PSEUDOMONAS CHLORORAPHIS* STRAIN NCIMB 40616

[75] Inventors: Berndt Gerhardson; Annika Gustafsson, both of Uppsala; Tiiu Jerkeman, Märsta; Britt-Marie Jingström, Björklinge; Lennart Johnsson; Margareta Hökeberg, both of Uppsala, all of Sweden

[73] Assignee: BioAgri AB, Stockholm, Sweden

[21] Appl. No.: 08/722,154

[22] PCT Filed: Apr. 13, 1995

[86] PCT No.: PCT/SE95/00408

§ 371 Date: Jan. 17, 1997

§ 102(e) Date: Jan. 17, 1997

[87] PCT Pub. No.: WO95/28085

PCT Pub. Date: Oct. 26, 1995

[30] Foreign Application Priority Data

Apr. 18, 1994 [SE] Sweden .................. 9401307

[51] Int. Cl.[6] .......... A01N 63/00; A01N 25/00; C12N 1/20; C12N 1/00
[52] U.S. Cl. ............. 424/93.47; 424/93.4; 424/405; 435/253.3; 435/874
[58] Field of Search ................ 424/405, 93.4, 424/93.47; 435/253.3, 874

[56] References Cited

U.S. PATENT DOCUMENTS 5,244,658  9/1993  Parke ...................... 504/117
5,512,466  4/1996  Klee et al. ................. 435/172.3

OTHER PUBLICATIONS

Ronquist, *VÄXTSKYDDSNOTISER*, vol. 58, No. 2, 1994, 42–44.
Berg et al., STN International, File Biosis, STN accession No. 94:551790.
Xiangpeng et al., STN International, File CA, *Chemical Abstracts*, vol. 98, No. 3, Jan. 17, 1983, abstract No. 14103.
Raaska et al., STN International, File CABA, *CAB Abstract*, vol. 94, 19991, abstract No. 1076.
Norinsho, STN International, File WPIDS, STN accession No. 93–410750.
Fujisawa Pharm Co Ltd, STN International, File WPIDS, STN accession No. 91–255505.
Ronquist, "Seed Treatmt W/ . . . "1994, See Abstract An 95:164651 Biosis. Abstract Only.

*Primary Examiner*—Leon B. Lankford, Jr.
*Assistant Examiner*—Deborah K. Ware
*Attorney, Agent, or Firm*—Bacon & Thomas

[57] ABSTRACT

A pure culture of *Pseudomonas chlororaphis* strain NCIMB 40616 is disclosed. The strain is useful for a biocontrol composition for the control of plant fungal diseases. Further, a culture broth of the strain is disclosed to be useful wherein antipathogenically active metabolites are contained in the culture broth. In addition a method of controlling the plant fungal diseases is disclosed which is carried out by the introduction of an effective dose of the strain into a plant environment infected with fungal diseases. Also carriers and additives are admixed with the strain in order to provide for the composition. The types of pathogenic fungi which may be controlled using the method and composition are of the genera Drechslera, Microdochium, Tilletia or Ustilago.

18 Claims, 1 Drawing Sheet

COMPOSITION AND METHOD FOR CONTROLLING PLANT DISEASES USING *PSEUDOMONAS CHLORORAPHIS* STRAIN NCIMB 40616

FIELD OF THE INVENTION

The present invention relates to plant protection products. More specifically, the invention relates to a novel strain of the bacterial species *Pseudomonas chlororaphis* and the use of compositions containing this bacterial strain or antibiotic substances produced by this strain in plant production in order to protect plants against attacks by phytopathogenic microbial agents.

BACKGROUND OF THE INVENTION

Several agents of microbial nature with the ability to induce plant diseases cause considerable damages, and accordingly economic losses, in crop plants. Many of them attack leaves and/or other aerial plant parts and then usually reach new uninfected crops by airborne spores. Others are transmitted from one crop generation to the next by being seedborne and several economically important disease-inducing agents are soilborne and reside more or less inactive in the soil until a susceptible crop is grown.

Procedures exerted for controlling microbial disease-inducing agents in crop production are often costly, but in most crop growing systems economically necessary. One widely used method is treatment with biostatic or biocidal chemicals. They are in most cases applied as sprays on growing crops, as seed or root treatments or as soil disinfectants. Other standard methods are breeding for resistance and management of the cropping system itself.

These standard control methods all have some drawbacks. Managing of the cropping system is effective or convenient only for certain disease problems. Also the breeding of crop plants for resistance is possible or suitable only in certain cases, may take long time and the resistance obtained may be broken after some time by the appearance of new strains of the pathogen. Chemical compounds often are highly effective, but they may give unwanted effects in the environment, require careful handling as most are risky for human health and they also may become ineffective where resistant pathogen strains develop.

The use of biological control agents or biopesticides may be more effective or more preferable than the use of other control methods and, thus, such agents have been extensively tried. Several bacterial and fungal strains are known to inhibit growth of various microbial disease-inducing agents. To be effective and usable they have to be stable, give reproducible results in the field and there must be possibilities to apply them under field conditions. To date few have fulfilled these requirements and, thus, have been used as commercial products.

BRIEF DESCRIPTION OF THE INVENTION

The present invention provides a biological control agent useful and effective for controlling plant pathogen attacks in commercial plant growings. A novel strain (MA 342) of the bacteria *Pseudomonas chlororaphis* showing the desired characteristics is provided. The isolate was deposited at the National Collections of Industrial and Marine Bacteria Limited (NCIMB), Aberdeen, Scotland on Feb. 14, 1994 under the terms of the Budapest Treaty and has received NCIMB Accession No. 40616.

The invention also provides a plant disease controlling composition containing as active ingredient the novel strain MA 342 or mutants thereof with essentially the same characteristics or antipathogenically active metabolites or derivates thereof. Further, the invention provides a method of controlling plant diseases using the novel strain MA 342 or mutants thereof with essentially the same characteristics or antipathogenically active metabolites or derivates thereof.

DETAILED DESCRIPTION OF THE INVENTION

Figure 1:
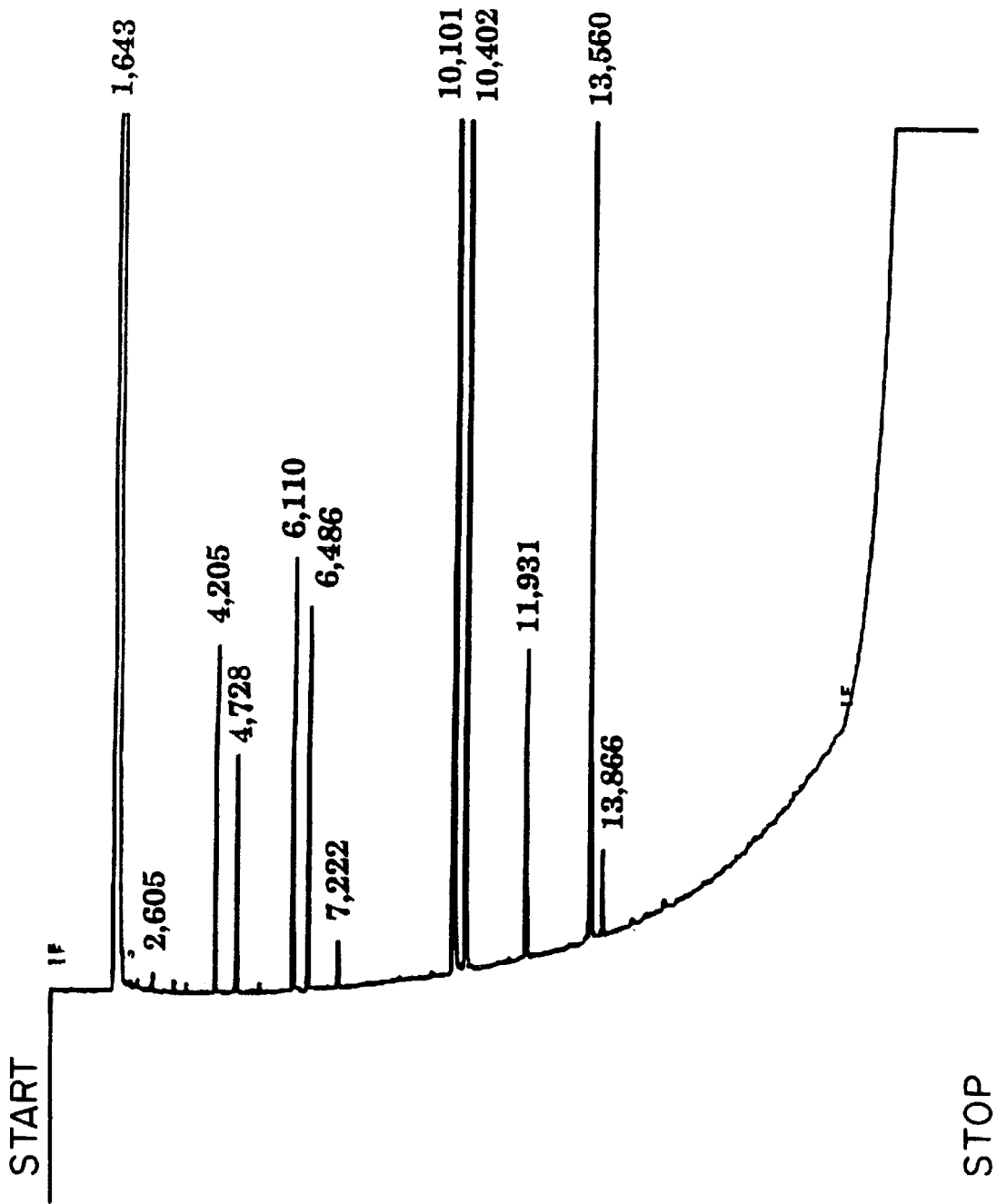
FIG. 1: This figure shows the fatty acid profile obtained with the Microbial Identification System (MIDI, Newark Ltd., USA) of the bacterial isolate MA 342.

Below follows a characterization of the novel bacterial strain and a description of preferred methods for strain proliferation and for formulations and applications in the field or in greenhouses. Several examples are offered to further illustrate, but not to limit, the method and composition of the invention.

Characterization of the novel bacterial strain MA 342

Morphological characteristics:

Colony morphology on TSA 10 (10 g Tryptic Soy Broth (Difco Ltd.); 12 g Technical Agar (Oxoid Ltd.) in 1000 ml distilled water) is round, white, moderately convex colonies that form well visible hyaline crystals in the agar at high cell densities. It is a Gram negative rod that shows a bright 1000 ml distilled water).

Fatty acid analysis:

The fatty acid profile of the bacterium is shown in FIG. 1. This analysis was performed using the Microbial Identification System (MIDI Ltd., Newark, USA), version 3.7. According to this test program, MA 342 is most similar to *Pseudomonas chlororaphis*, with a matching index of 0.705.

| Biochemical characteristics | |
| --- | --- |
| Characteristics tested in API 20 NE* rapid test | Reaction of isolate MA 342 |
| Nitrate reduction | − |
| Indole production | − |
| Acid from glucose | − |
| Arginine dihydrolase | + |
| Urease | − |
| Esculin hydrolysis | − |
| Gelatin hydrolysis | + |
| B-galactosidase | − |
| Glucose assimilation | + |
| Arabinose assimilation | − |
| Mannose assimilation | −? |
| Mannitol assimilation | + |
| N-acetyl-glucosamine assimilation | − |
| Maltose assimilation | − |
| Gluconate assimilation | + |
| Caprate assimilation | − |
| Adipate assimilation | − |
| Malate assimilation | + |
| Citrate assimilation | + |
| Phenyl-acetate assimilation | − |
| Cytochrome oxidase | + |
| Characteristics tested in additional tests | |
| Levan production | − |
| Xylose assimilation | −? |
| Sorbitol assimilation | +? |

*API System Ltd., France

Preferred methods for strain proliferation and for formulations and applications in the field or in greenhouses Quantities of the active strain is best obtained by a fermentation process that comprises inoculating a sample of a pure culture of the strain into a liquid shake culture or in a fermentor containing a suitable fermentation medium. The strain may also be grown on a sterile surface, e.g. an agar surface, and when grown out, the cells may be suspended in water or other liquid media known in the art. Growing media may in principle be any bacterial growth medium known in the art. The fermentation is carried out until a sufficient concentration of cells, e.g. about $5-10^9$ cfu (colony forming units)/ml for liquid cultures, is obtained. The so obtained fermentation broth or bacterial suspension may be employed as such for use in plant protection, or they may be treated or formulated before being used.

In one type of treatment the bacterial cells in the fermentation broth may be killed, e.g. by heating, or centrifuged down and the resulting broth or supernatant, containing bacterial metabolites, may be used for plant protection purposes, with or without prior purification and/or concentration. Bacterial suspensions and fermentation broths may also be homogeneously mixed with one or more compounds or groups of compounds known in the art, provided such compounds are compatible with the bacterial strains or its antipathogenically active metabolites or derivates of these. Suitable compounds may be powdery additives or solid carriers, such as talcum, kaolin, bentonite or montmorillonite, wettable powders known in the art, carbon source nutrients (such as glucose, sucrose and fructose) or complex bacterial nutrients (such as yeast extract, bacteriological peptone and tryptone), metal salts, salts from fatty acids, fatty acid esters, ionic or non-ionic surfactants, plant nutrients, plant growth regulators, fungicides, insecticides, bactericides and the like. Bacterial suspensions and fermentation broths may also be dried or freeze-dried prior to or after being mixed with suitable compounds and the resulting product used for plant protection. A suitable way of drying is for example air drying of vermiculite supplied with bacterial fermentation broth.

Bacterial and metabolite preparations may be applied in any manner known for treating seeds, vegetative propagation units, plants and soil with bacterial strains. Spraying, atomizing, dusting, scattering, pelleting, dipping or pouring may be chosen in accordance with the intended objective and the prevailing circumstances. Advantageous rates of application for seed treatment are normally from $10^{11}$ to $10^{12}$ cfu/ha and for spraying $10^{12}$ to $10^{14}$ cfu/ha or a corresponding amount of bacterial metabolites.

EXAMPLE 1

Isolation of the Microorganism MA 342

The dug up roots of the plant *Empetrum nigrum* were washed in sterile tap water to remove adhering soil. From a young root a piece, 2–3 cm long, was cut out and handled under sterile conditions. The piece was taken from the region above the root tip area. Small cuts were made in the root piece with a flamed scalpel. The root piece was then rubbed against the surface of TSA 10 agar. After bacteria had grown out, MA 342 was picked and was pure cultured on to TSA 10.

EXAMPLE 2

Preservation of the Microorganism MA 342

The Pure culture was deep frozen in small ampoules at $-70°$ C. As freeze protecting agent were used 10% glycerol in tap water, pH adjusted to 7.15 after autoclaving. After freezing at $-70°$ C., the ampoules were stored at $-20°$ C.

For long term preservation the isolate was freeze dried. After growing for 48 hours on TSA 10 agar, the bacterial lawn was scraped off the agar surface, mixed with a freeze drying protecting agent (50 g Dextran T 70 (Pharmacia Fine Chemicals Ltd.); 50 g Na-L-glutamate (Kebo AB) in 1000 ml of distilled water), poured into small ampoules (20 ml) and put in a Hetosicc freeze drier (Heto Ltd., Denmark) for 24 hours. After freeze drying the ampoules were gas tightly sealed with rubber stoppers and stored at $4°$ C.

EXAMPLE 3

Effect of MA 342 against *Microdochium nivale* in primary greenhouse screenings

The bacterium was applied to the seeds of wheat as follows: 24 hours old cultures on TSA 10, grown at $15°$ C., were scraped off from the agar surface of a 9 cm Petri dish and mixed with 40 ml of nutrient broth (SNB: 18 g sucrose; 5 g bacterial peptone (Oxoid Ltd.); 2 g yeast extract (Oxoid Ltd.); 0.5 g $K_2HPO_4$ and 0.25 g $MgSO_4.7H_2O$ in 1000 ml distilled water and pH adjusted to 7.2–7.4) and 40 ml of a 2% (w/v) solution of sodium carboxymethyl cellulose (CMC) in sterile distilled water. This mixture was poured over the seeds. After 20 minutes the excess mixture was poured off and the seeds were dried under a fan overnight.

For each treatment in this greenhouse screening two pots were sown with 50 seeds in each pot. The pots were 18 cm in diameter and 4 cm high and filled to two thirds with an unsterilized commercial peat mixture (Enhetsjord K Normal), mixed with 20% (v/v) sand.

The winter wheat seeds (cv. "Kosack") were artificially infested with *M. nivale* prior to the treatment with bacteria. The pathogen was cultivated for seven days in potato dextrose broth (24 g Potato Dextrose Broth (Difco Ltd.) per 1000 ml distilled water) at room temperature on a rotary shaker. The resulting slurry was homogenized with a kitchen blender and poured over the seeds. After 30 minutes the liquid was poured off and the seeds were left to dry under a fan over night. Seeds thus infested were then treated with MA 342 and sown in pots as described above.

After sowing, the pots were covered with glass lids and placed in the dark at $6°$ C. After five days the lids were removed, each pot watered with 100 ml of water and placed inside a five liters plastic bag that was supported by two wooden sticks. The pots were then placed in a greenhouse at $12-15°$ C. for eight days.

The following treatments of seeds were tested:
1. *P. chlororaphis* strain MA 342, mixed with SNB/CMC, on *M. nivale*-infested seeds
2. *M. nivale*-infested seeds, as disease control
3. Untreated seeds as healthy control The disease suppressive effect was recorded as the percentages of emerged, healthy (=without mycelia) plants out of those sown. Results from a typical *M. nivale* primary screening is shown in table 1.

TABLE 1

Effect of MA 342 on emergence and disease development in winter wheat, raised from *M. nivale*-infested seeds

| Treatment | Percentage (%) emergence | Percentage (%) healthy plants out of those sown |
|---|---|---|
| 1. MA 342 | 87 | 81 |
| 2. Disease control | 13 | 7 |
| 3. Untreated control | 90 | 89 |

EXAMPLE 4

Effect of MA 342 against *Drechslera teres* in secondary greenhouse screenings

For these screenings the isolate MA 342 was grown for 48 hours in half strength (15 g/l) Tryptic soy broth (Difco Ltd.)

on a rotary shaker in the dark at 18–20° C. Seeds of the barley cultivar "Golf", naturally infected with *D. teres*, were then mixed with 300 ml of the resulting bacterial suspension per kg seed in a plastic bag and, after mixing, the bag was shaken for about 4 minutes. Seeds thus treated were dried under a fan at room temperature for one day and then sown in pots as described in Example 3.

The sown pots, three per treatment, were placed first in the dark at 6° C. for seven days and then in a greenhouse at about 20° C. as described in Example 3. For reading treatment effects the frequency of germinated plants and the frequency of plants with primary attack on the first leaf were counted. The bacterial effect was related to an untreated control and seeds treated with the fungicide Panoctine Plus 400 (guazatine 150 g/l+imazalil 10 g/l), Rhône-Poulenc Ltd., in a dosage of 4 ml per kg seed.

TABLE 2

Effect of MA 342 and of Panoctine Plus 400 against *D. teres* in barley in a typical greenhouse secondary screening

| Treatment | Percent germinated plants | Percent plants with attack on the first leaf |
| --- | --- | --- |
| Control | 92.5 | 13.0 |
| Panoctine Plus 400, 4 ml/kg | 95.5 | 0.0 |
| MA 342, 300 ml/kg | 96.1 | 0.0 |

EXAMPLE 5

Effect of MA 342 on plant pathogens in field experiments

Field experiments, designed as randomized blocks and with three to eight repetitions, had plot sizes varying between experiments from 0.15 $m^2$ (one *T. caries* experiment) to about 15 $m^2$ (most experiments). The experiments were placed at different localities in Sweden and in most cases on loamy soils with about 3 percent humus content.

Treatments of seeds with bacteria and with Panoctine Plus 400 were done as described in Example 4 above. After the treated seeds had been dried with a fan they were stored at room temperature for various times before they were sown in field plots. All seeds, except those infested with *T. caries*, were naturally infested or infected with the various diseases tested. Seeds of winter wheat (cv. "Kosack") were artificially infested with spores of *T. caries* by mixing 2 g crushed *T. caries*-ears with 1 kg wheat seeds.

Effect of MA 342 on *Tilletia caries*

The effect was read as the frequency of infected ears at time of ripening. Results obtained in two trials in 1991/92 and two trials in 1992/93 are shown in Table 3. The difference between bacterial treatment and the fungicide treatment is significant in 1992/93.

TABLE 3

Effect of MA 342 bacterial suspension against seed borne *Tilletia caries* infection

| | Percent infected ears | |
| --- | --- | --- |
| Treatment | 1991/92 | 1992/93 |
| Control | 23 | 65 |
| Panoct. 400*, 4 ml/kg | 2 | 24 |
| MA 342, 300 mg/kg | 0 | 9 |

*Panoctine 400 (guazatine 150 g/l), Rhône-Poulenc Ltd.

Effect of MA 342 on *Drechslera teres, D. raminea, D. avenae* and *Ustilago avenae*

In the field experiments with these pathogens the number of germinated plants per $m^2$ and the number of infected plants per $m^2$ were measured and, in addition, in most of the experiments also i) grain yield ii) thousand kernel weight and iii) weight per hectolitre.

Effect on *Drechslera teres*:

Results from field experiments conducted in 1991–1993 and where effects against *D. teres*-infection in barley were tested are shown in tables 4, 5 and 6.

TABLE 4

Results from four field experiments in barley infected with *Drechslera teres* in 1991. Means from four experiments conducted at Alnarp, Lanna, Strängnäs and Ultuna

| Treatment | Yield kg/ha | No. of plants/$m^2$ | Infected plants/$m^2$ | Hectolitre weight, kg | 1000-kernel weight, g |
| --- | --- | --- | --- | --- | --- |
| Control | 4970 | 361 | 47 | 64.7 | 41.5 |
| Pan. Plus 400, 4 ml | 5390 | 353 | 1 | 66.3 | 43.8 |
| MA 342, 300 ml/kg | 5480 | 353 | 1 | 66.0 | 43.7 |

TABLE 5

Results from five fields experiments in barley infected with *Drechslera teres* in 1992. Means from experiments conducted at Svalöf, Nygård, Kölbäck, Ultuna and Röbäcksdalen

| Treatment | Yield kg/ha | No. of plants/$m^2$ | Infected plants/$m^2$ | Hectolitre weight, kg | 1000-kernel weight, g |
| --- | --- | --- | --- | --- | --- |
| Control | 4290 | 358 | 48 | 67.9 | 51.7 |
| Pan. Plus 400, 4 ml | 4380 | 378 | 1 | 67.8 | 50.5 |
| MA 342, 300 ml/kg | 4300 | 380 | 1 | 68.3 | 52.6 |

TABLE 6

Results from two field experiments in barley infected with *Drechslera teres* in 1993. Means from the experiments conducted at Kölbäck and Ultuna

| Treatment | Yield kg/ha | Infected plants/$m^2$ |
| --- | --- | --- |
| Control | 6310 | 74 |
| Pan. Plus 400, 4 ml | 6730 | 1 |
| MA 342, 200 ml/kg | 6720 | 5 |

Effect on *Drechslera graminea*:

The results from experiments with *D. graminea*-infected seeds conducted in 1991–1993 are shown in tables 7, 8 and 9.

TABLE 7

Results from one field experiment in 1991 conducted in Uppsala in barley infected with *D. graminea*

| Treatment | Yield kg/ha | Infected plants/m² |
|---|---|---|
| Control | 3440 | 31 |
| Pan. Plus 400, 4 ml | 4160 | 2 |
| MA 342, 300 ml/kg | 4390 | 1 |

TABLE 8

Results from five field experiments conducted in 1992 in barley infected with *D. graminea*. Means from experiments conducted at Svalöv, Nygård, Kölbäck, Ultuna and Röbäcksdalen

| Treatment | Yield kg/ha | No. of plants/m² | Infected plants/m² | Hectolitre weight, kg | 1000-kernel weight, g |
|---|---|---|---|---|---|
| Control | 2590 | 383 | 101 | 66.2 | 40.2 |
| Pan. Plus 400, 4 ml | 3470 | 381 | 5 | 66.6 | 39.9 |
| MA 342, 300 ml/kg | 3460 | 368 | 7 | 66.2 | 39.8 |

TABLE 9

Results from two field experiments in 1993 in barley infected with *D. graminea*. Means from experiments conducted at Kölbäck and Ultuna

| Treatment | Yield kg/ha | Infected plants/m² |
|---|---|---|
| Control | 2810 | 46 |
| Pan. Plus 400, 4 ml | 4160 | 1 |
| MA 342, 200 ml/kg | 3990 | 8 |

Effect on *Drechslera avenae*:

The results from experiments with *D. avenae*-infected oats seeds conducted in 1991–1993 are shown in tables 10, 11 and 12.

TABLE 10

Results from one field experiment in 1991 conducted in Uppsala in oats ("Puhti") infected with *D. avenae*

| Treatment | Yield kg/ha | Infected plants/m² |
|---|---|---|
| Control | 4940 | 74 |
| Pan. Plus 400, 4 ml | 4860 | 32 |
| MA 342, 300 ml/kg | 5090 | 17 |

TABLE 11

Results from four field experiments in 1992 in oats ("Puhti" and "Vital") infected with *D. avenae*. Means from experiments conducted at Svalöv and Ultuna

| Treatment | Yield kg/ha | No. of plants/m² | Infected plants/m² | Hectolitre weight, kg | 1000-kernel weight, g |
|---|---|---|---|---|---|
| Control | 3990 | 428 | 22 | 57.5 | 35.4 |
| Pan. Plus 400, 4 ml | 4080 | 456 | 13 | 57.8 | 35.5 |
| MA 342, 300 ml/kg | 4000 | 445 | 3 | 57.4 | 35.0 |

TABLE 12

Results from a field experiment in 1993 conducted in Uppsala in oats ("Vital") infected with *D. avenae*

| Treatment | Yield kg/ha | Infected plants/m² |
|---|---|---|
| Control | 7570 | 79 |
| Pan. Plus 400, 4 ml | 7870 | 14 |
| MA 342, 200 ml/kg | 7680 | 27 |

Effect on *Ustilago avenae*:

In the field experiments with *U. avenae* bund ears per m² or percentage of bunt ears were read at the time of ripening. Grain yield was not measured. Results from three experiments conducted 1991–1993 are shown in Table 13.

TABLE 13

Results from three field experiments conducted in 1991–1993 in Uppsala in oats infected with *Ustilago avenae*

| Treatment | 1991 Bunt ears/m² | 1992 % infected ears | 1993 Bunt ears/m² |
|---|---|---|---|
| Control | 7 | 10,6 | 95 |
| Panoctine Plus 400, 4 ml | 3 | 8,7 | not tested |
| MA 342, 300[1)] ml/kg | 1 | 1,7 | 15 |

[1)]300 ml 1991 and 1992; 200 ml in 1993.

EXAMPLE 6

Application of MA 342 to seeds and other plant parts

Applying aqueous mixtures containing MA 342 to seeds.

Bacterial suspensions produced as described in example 3 or as described in example 4 above were mixed with each of the following substances or compounds:

Talcum powder (Kebo Lab AB), 48 g/l of bacterial suspension

Bacteriological peptone (Oxoid, Ltd.), 5 g/l of bacterial suspension

Tween 20 (Merck Ltd.), 20 ml/liter of bacterial suspension

Metocel (Cellulose ether, Sveda Kemi AB), 12 g per liter of bacterial suspension Lissapol (ICI Agrochemicals Ltd.), 1 g per liter of bacterial suspension Bond (Newman Agrochemicals Ltd.), 1 g per liter of bacterial suspension In other experiments the bacterial suspensions were centrifuged at 10,000× g for about 10 min. and the resulting pellets were resuspended in either 0.1 M $MgSO_4$ or in peptone water (5 g of bacteriological peptone (Oxoid, Ltd.) per liter of tap water).

After thoroughly mixing, the resulting suspensions were applied to seeds as described in example 4 for unmixed bacterial suspensions.

Applying freeze-dried bacteria to plant seeds.

MA 342 bacteria, grown in a shake culture as described in example 4 above, were centrifuged and the resulting pellet was resuspended in a skim milk solution (200 g skim milk powder, Semper AB, Sweden, per liter of sterile distilled water) as a freeze drying protecting agent. The mixture was shell frozen in glass jars and then freeze dried in these jars for about 48 hours in a Hetosicc freeze drier (Heto Ltd., Denmark). The resulting powder was stored at 4° C. in plastic bags or in plastic flasks with a screw cap until used. For seed application the powder was either mixed in water or in other aqueous solutions and then applied to seeds as described in example 4 for bacterial suspensions, or it was mixed with seeds in a dry condition by thoroughly shaking the powder and the seeds (about 10 g powder per kg seed) in a plastic container.

Pelleting seeds treated with MA 342.

MA 342 bacteria, grown in a shake culture as described in example 4 above, were mixed in volumes 1:1 with an adherent (2% w/v aqueous solution of sodium carboxymethyl cellulose or 50% w/v aqueous solution of gummi arabicum). The seeds were treated with this mixture as in example 4 above. An excess amount of bentonite (Dresser Minerals Inc.) or talcum powder (Kebo Lab AB) was then added to the plastic bag, the bag was inflated and vigorously shaken for a couple of minutes. After this the seeds were spread out on big trays under a fan and allowed to dry in room temperature.

Spraying plant shoots with bacterial suspensions.

MA 342 bacteria, grown in a shake culture as described in example 4 above, were filled in plastic hand sprayers or in a powered sprayer and then sprayed on to plant leaves and shoots. In other treatments the bacteria were first centrifuged at about 10.000× g for ten minutes, the pellet was resuspended in tap water and this resulting bacterial suspension was used for the spraying of plant leaves and shoots.

EXAMPLE 7

Effects of purified metabolites from MA 342 against diseases caused by *Drechslera teres* in greenhouse experiments.

The isolate MA 342 was grown for 48 hours in half strength (15 g/l) Tryptic soy broth (Difco Ltd.) on a rotary shaker in the dark at 18–20° C. The resulting bacterial suspension was centrifuged at 48,000 g for 30 min. and metabolites in the supernatant was then further purified with Sep-pak C 18 cartridges (Waters Associates) as follows:

1. 80 ml of supernatant was added to a Sep-pak activated with 10 ml methanol.
2. The Sep-pac was washed first with 5 ml 30% ethanol and then with 5 ml 40% ethanol.
3. The metabolites were eluted by 5 ml 70% ethanol.
4. The 70% ethanol-eluate was evaporated in a rotation-evaporator until about 1.5 ml water solution was left. It was then diluted with tap water up to a volume of 6.5 ml.

Seeds of the barley cultivar “Golf”, naturally infected with *D. teres*, were submerged in this 6.5 ml water solution of the metabolites for 30 minutes and were then sown in pots with 50 seeds per pot. The pots were covered with glass lids and placed in the dark at 6° C. After nine days the lids were removed and the pots were placed in a greenhouse at 15–22° C. for about two weeks. Germinated plants and disease attacks were then read as described in Example 4 above. As controls were used 1) untreated seeds and 2) seeds treated with supernatant not purified with Sep-pac and containing MA 342 cells.

TABLE 14

Effect of purified metabolites from MA 342 and supernatant containing MA 342 cells against *D. teres* in barley in a typical greenhouse testing

| Treatment | Percent germinated plants | Percent plants with attack on the first leaf |
|---|---|---|
| Untreated control | 97,0 | 21,6 |
| Supernatant with MA 342 cells | 99,0 | 1,0 |
| Evaporated cell-free eluate | 99,0 | 0,0 |

EXAMPLE 8

Results of comparative tests of MA 342 isolate and 11 other isolates of *Pseudomonas chlororaphis* received from different culture collections Eleven different non-Swedish isolates of *Pseudomonas chlororaphis* having the designations stated in Table 15 were tested, together with MA 342 isolate, for effect against leaf spot disease in barley and for inducing reactions in biochemical tests according to the test system API 20 NE. In addition, the isolates were compared for colony appearance and crystal formation on agar plates. The 11 non-Swedish isolates were from different countries and are deposited in four different well-reputed culture collections (Table 15).

Test of disease-inhibiting ability in greenhouse tests

The tests were conducted with *Drechslera teres*-infected barley, as described in Example 4, and all isolates were tested simultaneously i order to achieve an adequate comparison. As is evident from Table 15 the results show that MA 342 is clearly unique in the sense that no one of the other isolates tested herein has the property like MA 342 in this kind of test, viz. the ability to inhibit infection by *Drechslera teres*.

TABLE 15

Designations, country of origin and effects of MA 342 and 11 other *P. chlororaphis* isolates against *D. teres*-infection in barley in greenhouse tests

| Isolate designation | Country of | Effect on leaf spot in greenhouse tests. Percentage of infected plants after treatment with the isolate in question |
|---|---|---|
| MA 342 | Sweden | 9 |
| USDA B2075 | Czechoslovakia | 53 |
| USDA B1869 | New Zealand | 60 |
| USDA B14874 | USA, Colorado | 56 |
| USDA B14869 | USA, Illinois | 58 |
| USDA B1854 | USA, Louisiana | 43 |
| NCTC 10686 | England | 54 |
| NCTC 7357 | England | 58 |
| DSM 6508 | Germany | 56 |
| ATCC 9446 | USA | 61 |
| ATCC 17414 | USA | 50 |

TABLE 15-continued

Designations, country of origin and effects of MA 342 and 11 other
P. chlororaphis isolates against D. teres-infection in barley in
greenhouse tests

| Isolate designation | Country of | Effect on leaf spot in greenhouse tests. Percentage of infected plants after treatment with the isolate in question |
|---|---|---|
| ATCC 7811 | USA | 58 |
| Untreated control | | 71 |

Induction of reactions in biochemical tests
according to test system API 20 NE

The tests were carried out as described above. The results are shown in Table 16. They show that MA 342 also in this respect is unique can be differentiated from the other 11 isolates tested. Some of the isolates tested may not, according to this test, be considered to be central within the species *Pseudomonas chlororaphis*.

TABLE 16

Induced reactions by the different isolates tested in a number of biochemical tests according to the test system API 20 NE. A "+" represents a positive reaction and a "−" no/negative reaction.

| Property tested in API 20 NE test | MA 342 | B 2075 | B 1869 | B 14874 | B 14869 | B 1854 | NCTC 10686 | NCTC 7357 | DSM 6508 | ATCC 9446 | ATCC 17414 | ATCC 17811 |
|---|---|---|---|---|---|---|---|---|---|---|---|---|
| Nitrate reduction | − | − | + | − | − | + | + | + | + | + | + | + |
| Indole production | − | − | − | − | − | − | − | − | − | − | − | − |
| Acid from glucose | − | − | − | − | − | − | − | − | − | − | − | − |
| Arginine dihydrolase | + | + | + | + | − | + | + | + | + | + | + | + |
| Urease | − | − | − | − | − | − | − | − | − | − | − | − |
| Esculin hydrolysis | − | − | − | − | − | − | − | − | − | − | − | − |
| Gelatin hydrolysis | + | + | − | − | − | + | + | + | − | + | + | + |
| B-galactosidase | − | − | − | − | − | − | − | − | − | − | − | − |
| Glucose assimilation | + | + | + | + | + | + | + | + | + | + | + | + |
| Arabinose assimil. | − | + | + | − | − | − | + | − | + | − | − | − |
| Mannose assimilation | − | + | + | − | + | + | + | + | + | + | + | + |
| Mannitol assimilation | + | + | + | − | − | + | + | + | + | + | + | + |
| Glucosamine assimil. | − | + | + | − | − | + | + | + | + | + | + | + |
| Maltose assimilation | − | − | − | − | − | − | − | − | − | − | − | − |
| Gluconate assimilation | + | + | + | + | + | + | + | + | + | + | + | + |
| Caprate assimilation | − | + | + | + | + | + | + | + | + | + | + | + |
| Adipate assimilation | − | − | − | − | − | + | − | − | − | − | − | − |
| Malate assimilation | + | + | + | + | + | + | + | + | + | + | + | + |
| Citrate assimilation | + | + | + | + | + | + | + | + | + | + | + | + |
| Phenyl-acetate assimil. | − | − | + | + | + | + | + | + | + | − | − | + |
| Cytochrome oxidase | + | − | + | + | + | + | − | + | + | + | + | + |

Comparison of colony appearance and crystal
formation on agar plates

The isolates were cultured in Petri dishes on TSA 10, as described above. We observed small differences in colony appearance between all different isolates but all isolates could not be differentiated in this way. However, the MA 342 isolate was the only isolate forming typical hyaline crystals in the agar and could therefore, by this property, be differentiated from all other isolates.

What is claimed is:

1. A biologically pure culture of *Pseudomonas chlororaphis* strain NCIMB 40616 having the ability to produce antipathogenically active metabolites and mutants of said strain having all of the identifying characteristics of the strain NCIMB 40616.

2. A composition for controlling plant diseases caused by pathogenic fungi, which comprises as active ingredient the microorganism claimed in claim 1 or culture broth of said microorganism which contains antipathogenically active metabolites thereof.

3. The composition according to claim 2, wherein the pathogen is the fungus *Drechslera teres*.

4. The composition according to claim 2, wherein the pathogen is the fungus *Drechslera graminea*.

5. The composition according to claim 2, wherein the pathogen is the fungus *Drechslera avenae*.

6. The composition according to claim 2, wherein the pathogen is the fungus *Microdochium nivale*.

7. The composition according to claim 2, wherein the pathogen is the fungus *Tilletia caries*.

8. The composition according to claim 2, wherein the pathogen is the fungus *Ustilago avenae*.

9. The composition according to claim 2, wherein the active ingredient is in admixture with a carrier composition acceptable in agricultural practice.

10. The composition according to claim 9, wherein the active ingredient is in admixture with a liquid carrier.

11. The composition according to claim 9, wherein the active ingredient is impregnated in a solid porous material.

12. The composition according to claim 9, which further comprises additives that serve as adherents.

13. The composition according to claim 9, which further comprises a nutrient source.

14. A method of controlling plant diseases caused by pathogenic fungi and comprising the introduction of an effective dose of an active ingredient into the environment where the pathogenic fungi is to be inhibited, wherein the active ingredient is the microorganism claimed in claim 1 or culture broth thereof containing antipathogenically active metabolites or derivates thereof.

15. The method according to claim 14, wherein the active ingredient is applied to seeds.

16. The method according to claim 14, wherein the active ingredient is applied to plant vegetative propagation units.

17. The method according to claim 14, wherein the active ingredient is applied to plants.

18. The method according to claim 14, wherein the active ingredient is applied to a growing medium in which a plant is growing or is to be grown.

* * * * *